United States Patent [19]

Seppi et al.

[11] 4,066,901
[45] Jan. 3, 1978

[54] TOMOGRAPHIC SCANNING APPARATUS WITH IMPROVED COLLIMATOR STRUCTURE

[75] Inventors: Edward J. Seppi; Frederick V. Murphy, both of Menlo Park, Calif.

[73] Assignee: Varian Associates, Inc., Palo Alto, Calif.

[21] Appl. No.: 722,930

[22] Filed: Sept. 13, 1976

[51] Int. Cl.² .................. A61B 6/02; G01N 23/08; H05G 1/30
[52] U.S. Cl. .................. 250/360; 250/445 T; 250/511
[58] Field of Search .................. 250/505, 511, 445 T, 250/360

[56] References Cited
U.S. PATENT DOCUMENTS 2,331,586  10/1943  Waisco .................. 250/511

Primary Examiner—Alfred E. Smith
Assistant Examiner—T. N. Grigsby
Attorney, Agent, or Firm—Stanley Z. Cole; Leon F. Herbert

[57] ABSTRACT

An axial tomography system is disclosed which includes an assembly rotatable about an axis extending along a central opening defined therein, and means for positioning the body portion to be examined within the central opening so that the axis of assembly rotation is perpendicular to a plane passing through the bodily structures to be examined. A source of penetrating radiation is mounted on the assembly toward one side thereof and via a first collimating means provides radiation in the form of a fan beam. The first collimating means is mounted proximate to the radiation source, and includes an adjustable slit, which can be opened completely to enable a conventional x-ray exposure. Means are provided for rotating the assembly so that the fan beam impinges upon said body portion at a plurality of incident directions. Detector means for the radiation are positioned on the assembly opposite the source, enabling detection of radiation which traverses laterally and is not absorbed in the thin body section in which the aforementioned plane resides. The detector means is preferably of the ionization type, and may comprise an array of side-by-side cells. Second collimating means including a series of parallel plates overlie the detector means and assure that the radiation incident on each cell is substantially only that which has propagated along the radius of the fan beam which joins the cell to the radiation source. A third collimating means directly overlies the second, and comprises a slit extending transversely to the aforementioned plates.

3 Claims, 12 Drawing Figures

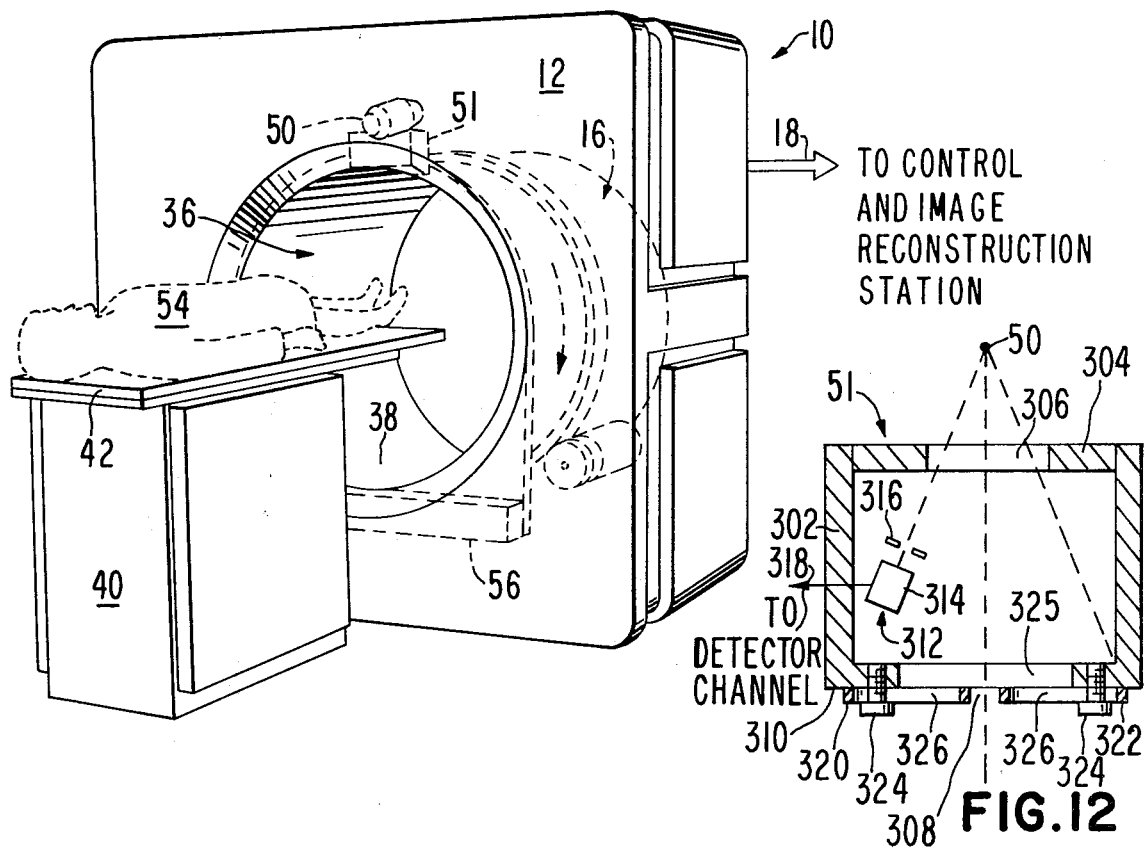
FIG. 1
FIG. 12
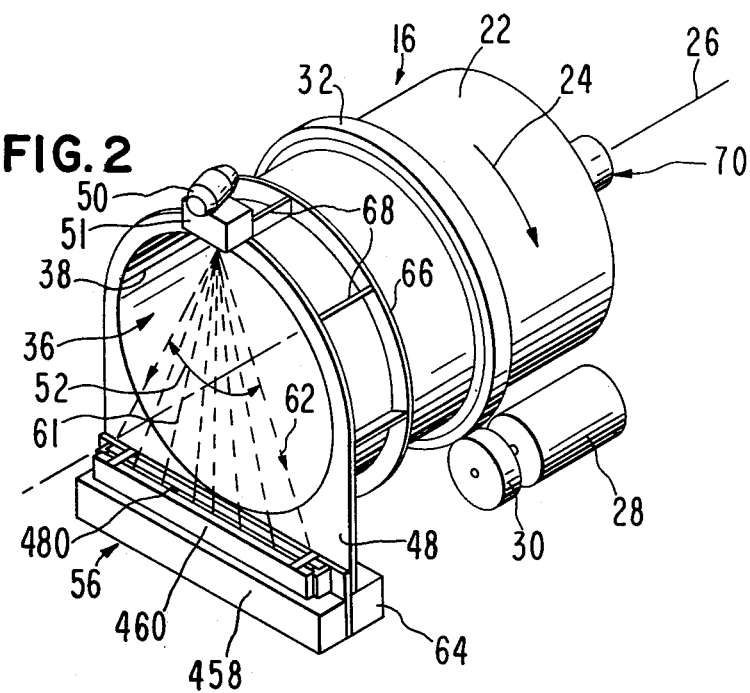
FIG. 2

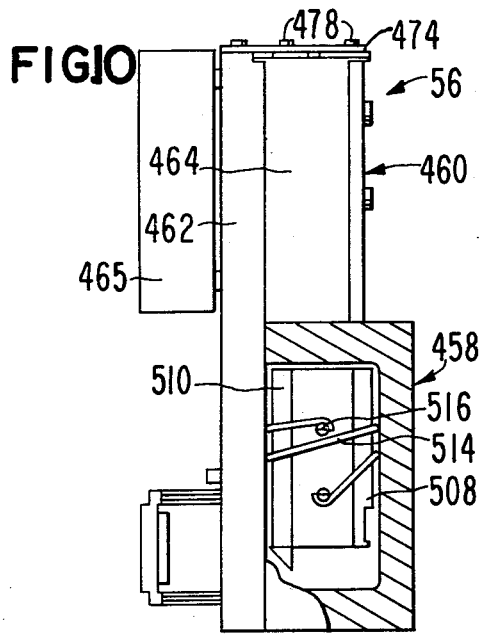
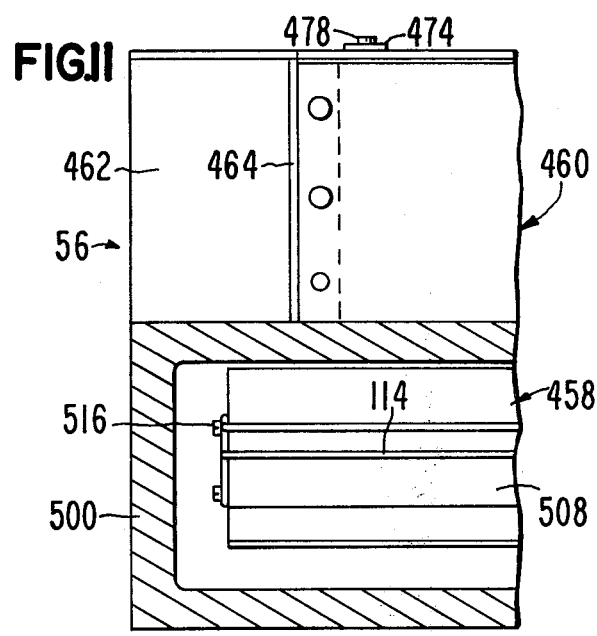
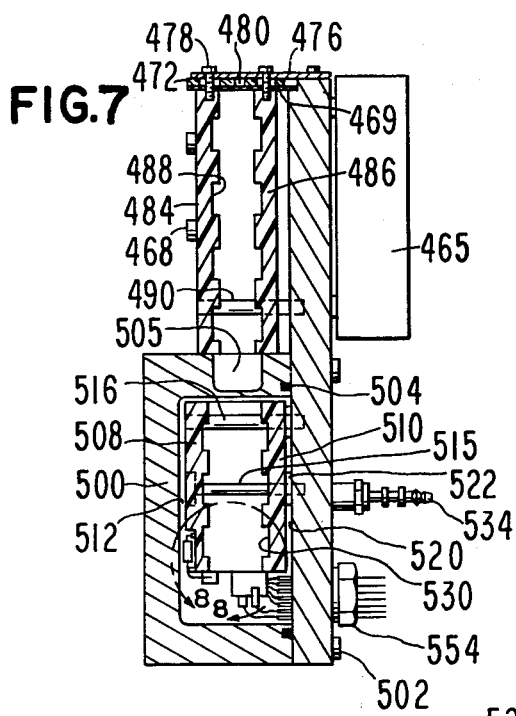
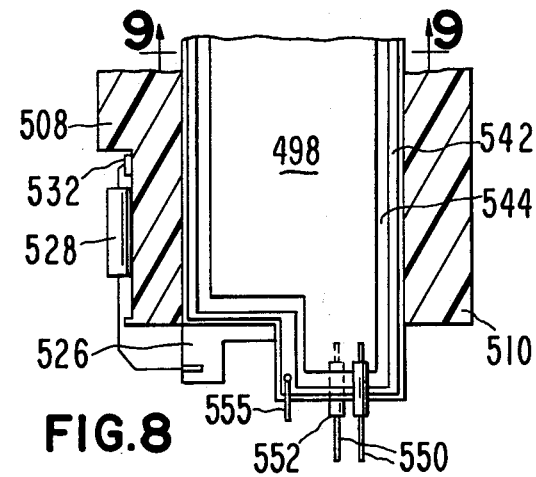
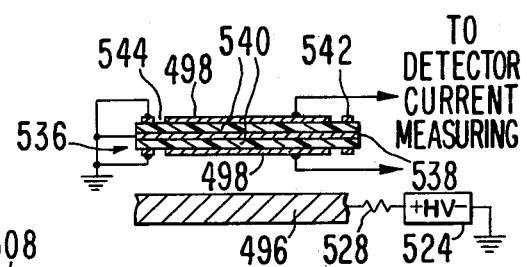
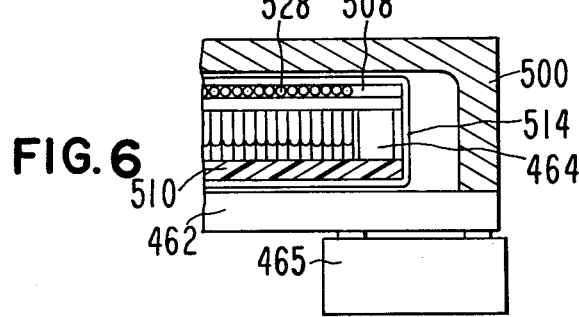

TOMOGRAPHIC SCANNING APPARATUS WITH IMPROVED COLLIMATOR STRUCTURE

BACKGROUND OF INVENTION

This invention relates generally to medical diagnostic apparatus and methodology, and more specifically relates to x-ray scanning apparatus of the type utilized in computerized tomography.

Within very recent years, a relatively enormous degree of interest has been evidenced on the part of medical diagnosticians in a field now widely known as computerized tomography. In a typical procedure utilized in computerized tomography (or CT), an x-ray source and detector means are positioned on opposite sides of the portion of the patient which is to be examined. In the prior art these paired elements are made to transit across the body portion to be examined, while the detectors measure the x-ray absorption at the plurality of transmission paths defined during the transit process. Periodically as well, the paired source and detector means are rotated to a differing angular orientation about the body, and the transit process repeated. A very high number of absorption values may be yielded by procedures of this type, and the relatively massive amounts of data thus accumulated may be processed by a digital computer — which crosscorrelates the absorption values to thereby derive absorption values for a very high number of points (typically in the thousands) within the section of the body being scanned. This point by point data may then be combined to enable reconstruction of a matrix (visual or otherwise) which constitutes an accurate depiction of the density function of the bodily section examined. The skilled diagnostician, by considering one or more of such sections, may diagnose various bodily elements such as tumors, blood clots, cysts, hemorrhages and various abnormalities, which heretofore were detectable, if at all, only by much more cumbersome and, in many instances, more hazardous (from the viewpoint of the patient) techniques.

While apparatus of the aforementioned type have therefore represented powerful diagnostic tools, and have been deemed great advances in the radiography art, apparatus heretofore designed and commercially available have suffered from many of the shortcomings incident to first generation devices. Thus, for example, it may be noted that acquisition of the raw data obtained as an incident of the discussed techniques frequently entailed an undesirably long period — which among other things subjected a patient to both inconvenience and stress. The patient's inability to remain rigid for such a lengthy period, also could lead to blurring of the image sought to be obtained.

In a copending application of John M. Pavkovich and Craig S. Nunan, Ser. NO. 643,894 filed on Dec. 23, 1975 entitled "Tomographic Apparatus and Method for Reconstructing Planar Slices from Non-absorbed Radiation", and as well in the similarly copending application of John M. Pavkovich entitled "Apparatus and Method for Reconstructing Data," filed on Dec. 23, 1975, under Ser. No. 643,896, both applications of which are assigned to the same assignee as is the present application, apparatus and methodology are disclosed which alleviate a number of the prior art problems, most notably including the lengthy period that has heretofore been involved in computer processing of the raw data provided by the detectors. The apparatus therein disclosed utilizes a fan beam source of radiation coupled with application of a convolution method of data reduction, with no intervening reordering of fan rays, to thereby eliminate the errors and delays in computation time which would otherwise be involved in such reordering. The radiation source and the detector means are positioned on opposite sides of the portion of the patient to be examined and these elements are made to rotate through a revolution or portion thereof while the detectors measure the radiation absorption at the plurality of transmission paths defined during the rotational process.

In apparatus of the above type, it is important to provide appropriate collimations for the x-ray or other radiation source. An initial requirement for collimation occurs adjacent the x-ray source — where the fan beam is established. A further requirement for collimation occurs at the detector cell array, where it is necessary to shield the individual cells from radiation reaching such cell from points in the fan beam which are removed from the radius extending between the cell and radiation source. In addition it is desirable to provide collimation for limiting the thickness of the fan beam.

SUMMARY OF THE INVENTION

Now in accordance with the present invention, scanning apparatus is provided which includes an assembly rotatable about an axis extending along a central opening defined therein, and means for positioning the body portion to be examined within a central opening so that the axis of assembly rotation is perpendicular to a thin, generally planar section of the body portion to be scanned. A source of penetrating radiation, as for example of x-rays or gamma rays, is mounted on the assembly toward one side thereof, and via a first collimating means, provides radiation in the form of a fan beam. Means are provided for rotating the assembly so that the fan beam impinges upon the body portion at a plurality of incident directions.

Detector means for the radiation are positioned on the assembly opposite the source, enabling detection of non-absorbed radiation proceeding laterally across the section. The detector means is preferably of the ionization type, and may comprise an array of side-by-side elongated cells, the principal axis of each cell being oriented along a radius extending toward the radiation source. A suitable atmosphere of a high Z gas such as xenon, krypton or xenon with krypton is maintained within the cell environment, typically at pressures of the order of about 10 atmospheres or higher. The plurality of such cells are located within a suitable enclosure to maintain the desired pressurization, and electrical feed-throughs pass through the said enclosure and are suitably insulated and sealed to enable application of high potential to plate members of the cells, and also to enable read out of the ionization current signals from other electrode members of the cells.

The aforementioned first collimating means is mounted proximate to the radiation source, and includes an adjustable slit which can be opened completely to enable a conventional x-ray. A second collimating means including a series of parallel plates overlie the detector means and assure that the radiation incident on each cell is substantially only that which has propagated along the radius of the fan beam which joins the cell to the radiation source. A third collimating means directly overlies the second, and comprises a slit extending transverse to the aforementioned plates.

Signal processing and conditioning means for receiving the output signals from the detector means and amplifying and converting such signals to digital form, are also mounted on the rotatable assembly adjacent to the detector and collimator assembly, and are movable with the rotatable assembly. The signals from the detector are therefore provided to the closely adjacent processing and conditioning means, which amplify and convert the signals provided thereto to a suitable form for further processing.

BRIEF DESCRIPTION OF DRAWINGS

The invention is diagrammatically illustrated, by way of example, in the drawings appended hereto in which:

FIG. 1 is an external perspective view, somewhat schematic in nature, of scanning apparatus in accordance with the present invention;

FIG. 2 is a perspective view, again somewhat schematic in nature, depicting the rotatable assembly portion of the FIG. 1 apparatus;

FIG. 6 is a partial view with the bottom removed, of the bottom of the said FIG. 4 apparatus;

FIG. 7 is a right end view of the FIG. 4 assembly, the said view being partially sectioned along the line 7—7 in FIG. 4;

FIG. 8 is an enlargement generally including the portion of FIG. 7 set forth within the dotted circle 8—8;

FIG. 9 is a cross-sectional view through the detector and high voltage plates of FIG. 8, the view being taken along the line 9—9 in FIG. 8;

FIG. 10 is a broken-away left end view of the FIG. 4 assembly, with the collimator portion thereof removed, and illustrating certain mounting features for the cell array; and FIG. 11 is a fragmentary plan view (broken-away) of the apparatus portions set forth in FIG. 9, and illustrates further details of the said mounting arrangement; and FIG. 12 is an enlarged cross-sectional view of the first collimating means, otherwise set forth in FIG. 3.

DESCRIPTION OF PREFERRED EMBODIMENT

Figure 3:
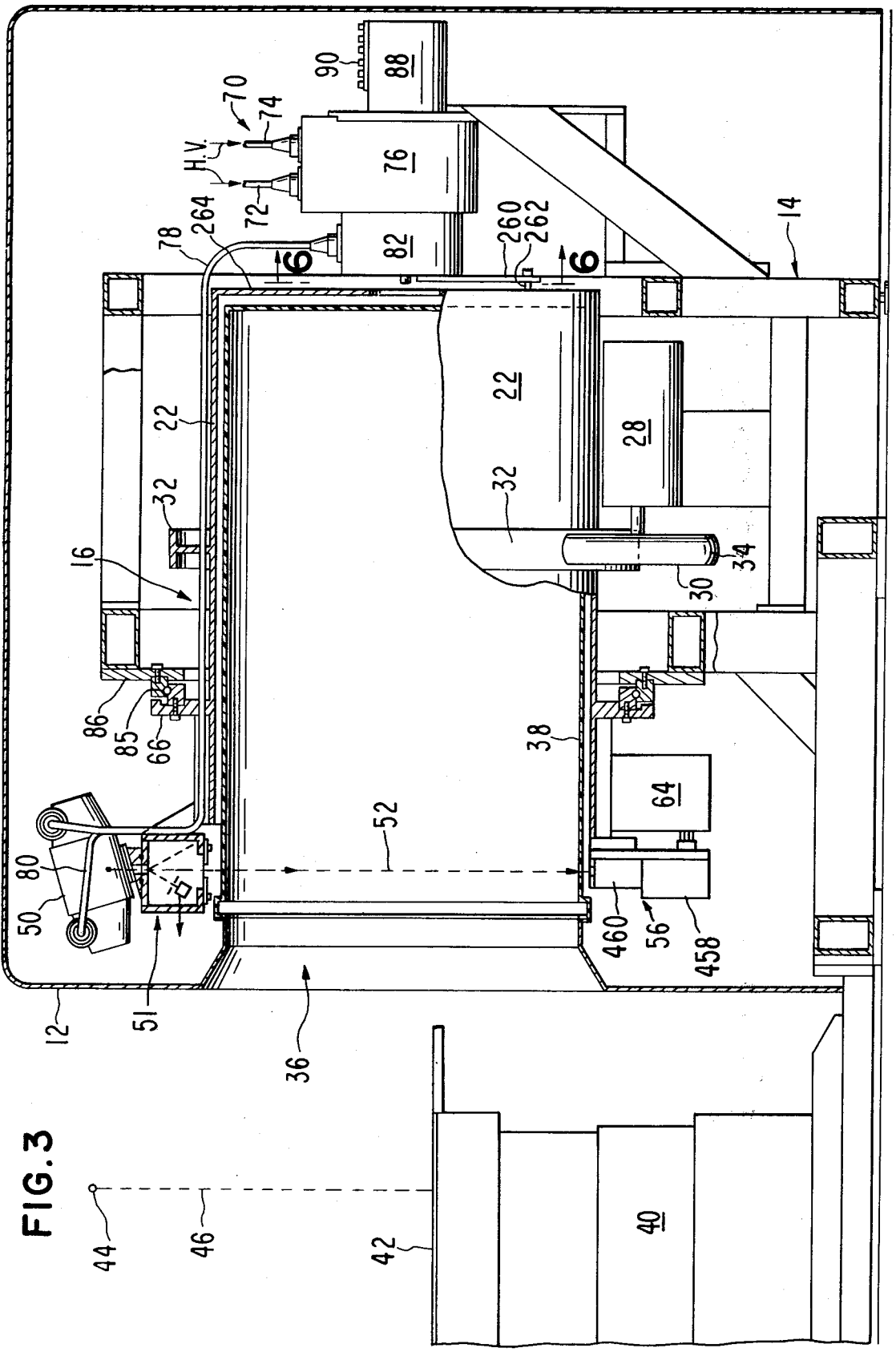
FIG. 3 is a side elevational view of the apparatus of FIGS. 1 and 2 therein, the view being partially broken away and in section.

In FIG. 1 herein an external perspective view appears, the view being somewhat simplified in nature and setting forth scanning apparatus 10 in accordance with the invention. This view may be considered simultaneously with the views of FIGS. 2 and 3. With certain exceptions, importantly including the collimator and detector assemblies (which will be fully discussed hereinbelow) apparatus 10 is substantially that disclosed in an application filed by Kendall L. Dinewiddie, et. al. on Apr. 19, 1976, under Ser. No. 677,958, and entitled "Tomographic Scanning Apparatus", which application is assigned to the same assignee as is the instant application.

Apparatus 10 is seen to comprise generally an external casing 12 within which a frame 14 (FIG. 3) supports a rotatable assembly 16, which assembly is better seen in FIG. 2. Scanning apparatus 10 forms part of a computerized tomography system, the remaining elements of which principally include control, image reconstruction elements, and image display elements, most of which are contained at a control and image reconstruction station — the details of which are not pertinent to the present invention. Apparatus 10 is in communication with the said station via various control lines, as schematically indicated at link 18 in FIG. 1, which is to say that digital information obtained in consequence of the scanning operations effected by apparatus 10 are furnished to such station; and the latter, in turn, provides both control information for actuating apparatus 10, as well as the various power and excitation potentials, e.g. for the radiation source, the motor, and other elements which are present in apparatus 10.

Rotatable assembly 16 includes an outer cylinder 22 of stainless steel or other metal, and is adapted to be rotated in direction 24 about its central axis 26, by means of a motor 28, the drive wheel 30 of which bears against a drive collar 32 which is secured about cylinder 22. Wheel 30 may thus include a rubber surface 34 or the like, which by virtue of its high coefficient of friction, is effective in causing non-slip rotation of cylinder 22.

By comparing FIGS. 1 and 2 it will be evident that the central opening 36 of rotatable assembly 16 serves to receive a patient 54 who is to be examined within apparatus 10. A sleeve 38 of plastic or the like is secured to casing 12, and provides a stationary reference frame which has certain advantages — especially psychologically for the patient who is positioned within opening 36.

The patient 54 during use of apparatus 10 is positioned upon the top surface 42 of a positioning bench 40, the surface 42 being movable along axis 26 so as to enable movement of the patient into the apparatus. A laser source 44 is positioned in front of apparatus 10 at an overhead position (FIG. 3) so that the beam 46 thereof impinges upon the patient at an axial location — to aid in proper alignment of the patient during the examination process. The laser may also be affixed to portions of casing 12. The bench 30 may include actuating means which enable incremental advance of same, so as to facilitate successive transverse scan sections through the body of patient 54, and which also enable movement of the bench in other directions to facilitate patient positioning.

The forward end of assembly 16 carries a plate 48, at the periphery of which is mounted a radiation source 50 — preferably comprising an x-ray source capable of projecting an x-ray pattern in the form of a fan beam 52. Fan beam 52 maybe yielded by a first collimating means which is positioned in front of the x-ray emission source (and will be further described hereinbelow). Fan beam 52 is preferably (though not necessarily) at least as wide as the object to be examined, which in the present instance, of course, constitutes patient 54.

The first collimating means 51 of FIG. 1 is better seen in the enlarged cross-sectional view of FIG. 12. As seen therein collimating means 51 comprises an enclosure 302, the upper side 304 of which is spaced from the x-ray source schematically indicated at 50. Upper side 304 is provided with a fixed relatively wide slot 306, which is aiigned with a further, adjustable slit 308 provided at the spaced lower side 310 of enclosure 302.

The interior of enclosure 302 carries an x-ray monitoring means 312, which may be one of two or more such devices mounted side-by-side in enclosure 302. These monitoring means include a detector 314, e.g. of the ionization or other type, and a suitable further collimator 316. The output 318 from monitoring means 312 is provided to a detector channel in signal processing and conditioning means 64, and is used to normalize the various detector signals, i.e. to enable compensation of such signals for variations in the intensity of x-ray source 50.

As mentioned, slit 308 at the lower side 310 of enclosure 302 is adjustable. Thus such slit may be defined by the spacing between plates 320 and 322 which cover a relatively wide slot 325 at lower side 310 of enclosure 302. Each plate 320 and 322 is fabricated of lead or similar radiation absorbing material and is secured to enclosure 302 by fasteners 324. Two or more such fasteners are used for each plate, although but a single one (per plate) can be seen in the plane of the drawing. The fasteners 324 pass through enlarged slots 326 in plates 320 and 322 and are threadingly engaged at enclosure 302. Accordingly one may adjust the size of the spacing between plates 320 and 322 — and thus of slit 308 — by loosening the fasteners and adjusting the lateral position of the plates toward or away from the center line therebetween. Equivalent constructions may also be utilized to enable the slit 308 adjustment — e.g. the two plates 320 and 322 may be mounted on tracks for sliding movement toward and away from each other by motorized adjustment; i.e. a gear actuated by such motion may thus displace the two plates by a simple gear and rack arrangement or so forth. The adjustment set in slit 308, in view of the much greater size opening provided by slot 306, will in part determine the "planar" width of fan beam 52. A further slit 480 which overlies detector-collimator assembly 56 is normally aligned with slit 308. The latter determines the ultimate "thickness" of the fan beam which is rendered incident on patient 54. Slip 480 determines the "thickness" of the fan beam incident on detector array 458.

One of the significant advantages deriving from the adjustability enabled in slit 308 is that by fully opening same, i.e. so that the source 50 is limited only by slot 325, the s-rays rendered incident on patient 54 are no longer in a thin, quasi-planar beam, but rather are propagated in a beam having a cross-section transverse to the beam direction of propagation which includes both substantial width and breadth. Thus such radiation is incident over an enlarged portion of the patient — i.e. the radiation is incident essentially as in the conventional x-ray exposure utilized for taking conventional radiographs. This is useful in that the physician may desire to obtain such conventional x-ray pictures; and to do so he need only appropriately position the patient, provide an x-ray sensitive plate beneath the patient; and, after fully opening slit 308, make the customary exposure.

A collimator-detector assembly generally indicated at 56, and consisting of a detector means 458 and a second collimator means 460, is mounted directly opposite source 50, i.e. toward the opposite edge of plate 48. Although other types of detectors suitable for use with x-rays and similar electromagnetic radiation may be utilized, such as crystal scintillators coupled with photomultipliers or photodiodes or soforth, detector means 458 preferably comprises an array of ionization chambers, such as xenon or xenon-krypton detectors.

It will be seen that detector means 458 is in very close physical proximity to a signal processing and conditioning means, generally indicated at 64. Indeed, in the apparatus depicted these two blocks are back to back with respect to one another. This close physical proximity has important advantages in the present environment in that the close proximity of these elements — which are commonly rotatable with assembly 16 — minimizes the possibility of introducing spurious signals into the various detector channels. This is particularly significant in the present instance in that the high potentials associated with the x-ray source, etc. increases the likelihood of introducing such spurious signals.

The assembly 16 in addition to including the several elements thus far described, includes certain strengthening elements such as the reinforcing ring 66 and cross braces 68. The purpose of these several elements is to increase, to the extent practical, the rigidity of the overall assembly 16, thereby decreasing the effects of vibration and the possibility of undesired flexure, all of which can be particularly detrimental with respect to the detector structures — i.e., stressing of certain of these structures can change the electrical response characteristics of same, thereby introducing erroneous readings.

In the case of x-ray diagnosis the thickness of fan beam 52 as defined by the collimators is typically between 1 mm and 15 mm at the middle of the object. It will be understood that as the source-detector array undergoes relative rotation with respect to the patient (continuously where exact reconstruction is desired) over a time of approximately 1 to 15 seconds, readings of absorbed radiation are measured by detector means 56. The data acquisition may be completed during one relative revolution (i.e. 360°) of the system; the present system is also well adapted to acquire the data over the course of several revolutions — which can provide superior images because of the increased quantity of data. As further described in the aforementioned copending applications of Pavkovich, et. al. Ser. No. 643,894 and Dinwiddie, et. al. Ser. No. 677,958, data from detector means 56, after suitable processing and conditioning, is provided to a control and image reconstruction station where it is convolved, appropriately stored and later back-projected with other data to produce an output picture which is a replica of the thin cross-section of patient 54 which has been examined. It will of course be understood that the data need not be necessarily converted into a visually discernable picture; but can be expressed in other analytical forms, i.e. numerically or so forth.

As may be seen by consideration of FIG. 3, electrical interconnections to all portions of assembly 16 which require same, is effected via a slip ring assembly (details not shown) which is generally indicated at 70. In particular it will be observed that high voltage input lines 72 and 74 are provided to the casing portion 76 of assembly 70, which portion is stationary. The slip ring interconnection provides the required excitation connections to x-ray source 50 via the cables 78 and 80 which proceed from casing portion 82 of assembly 70. The latter, portion 82, rotates with rotating assembly 16, which is supported on bearing 85 between ring 66 and a frame ring 86. In particular, rotation of portion 82 is effected commonly with the cylinder 22 by means of a link 260 which is secured to portion 82 and engages a pin 262 which projects from the rearward side 264 of cylinder 22.

Similarly the various further low voltage interconnections, i.e. for the detector outputs, for the various low voltage control signals for the electrical elements mounted on plate 48, and for the low voltage inputs to source 50 (for the anode rotor), are all enabled by means of slip ring connections contained within portion 88 of slip ring assembly 70. Thus several of the external connections 90 appear at portion 88. The external casing of portion 88 is, of course, stationary.

Referring now to FIGS. 5 through 10, details are set forth of the collimator-detector assembly 56. Referring generally to the views of FIGS. 4 and 5, it is seen that assembly 56 consists of the detector means 458 which is separate from but maintained in fixed relationship to the overlying collimator means 460. The two are maintained in direct contact with one another, by being secured to a support plate 462 — in each instance by bolting means. Mounting blocks 465 are secured to plate 462, and in turn, enable collimator-detector assembly 56 to be secured to plate 48.

Second collimator means 460 comprises a pair of collimator support members 484, 486 which are maintained in spaced relationship by spacers 464, the members being secured to plate 462 by bolts 468. The upper side of means 460 is therefore generally open (except for a thin radiation-pervious plastic covering 469 which prevents dust and debris from entering) and serves to admit the incident radiation provided by fan beam 52. As best seen in the top view of FIG. 5, a pair of parallel strips 470 and 472 extend lengthwise across the top open portion of second collimator means 460 (in overlying relation to cover 469). The ends of these strips 470 and 472 are supported by a pair of brackets 474 and 476 via threaded members 478 which pass through the plates and thence into the top edges of support members 484 and 486. The openings in brackets 474 and 476 through which the fasteners pass are elongated, in consequence of which the width of the slit 480 defined between strips 470 and 472 may be adjusted. Strips 470 and 472 comprise a material which is very absorbing with respect to the incident x-ray radiation, as for example, lead, and accordingly the slit 480 serves as a third collimator means for the radiation beam proceeding toward detector means 458. By adjusting the aforementioned spacing between strips 470 and 472, one can adjust the thickness of the incident fan beam 52 — in order, e.g., to improve definition or so forth in the resultant x-ray image. As already mentioned, the slit 480 is aligned with slit 308 in first collimating means 51, and the adjustment in size openings in the two slits will normally be correlated to produce a desired thickness in the fan beam incident on the patient.

Figure 4:
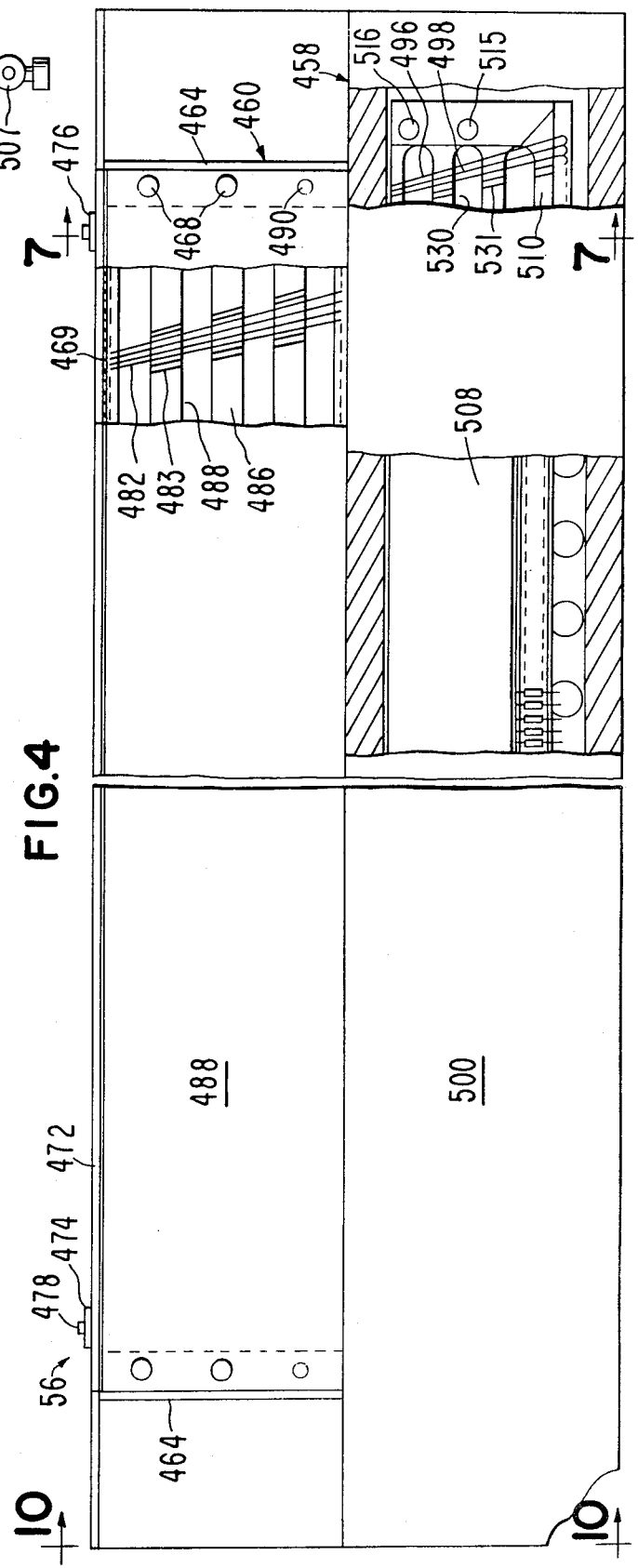
FIG. 4 is an elevational view of the detector assembly portion of the present apparatus, the view being partially broken away in order to illustrate certain interior details.

Referring to the broken-away portion of second collimator means 460 in FIG. 4, it will be seen that a plurality of collimator plates 482 are mounted in means 460 in a manner that will be further discussed below. In a typical embodiment of the present invention a total of 302 such mutually spaced collimator plates may be thus mounted. Each said plate is actually oriented so that its plane resides approximately along a radius proceeding to the x-ray source. The collimator plates 482 comprise a material which is highly absorbtive with respect to x-ray radiation, as for example, stainless steel or so forth, and such plates serve to further collimate the x-rays proceeding from source 50 toward a plurality of detector cells which are provided at detector means 458. Each such detector cell is oriented so that an overlying pair of spaced collimator plates 482 will direct the radiation passing therebetween in an axial direction through the associated detector cell.

By referring to the partially sectioned view of FIG. 7, it will be seen that the collimator plate support members 484, 486, which may comprise a composite fiberglass material or the like, include a series of parallel channels 488 which extend lengthwise along the inside face of each of the support means. Narrower channels or slots 483 are also formed in a vertically inclined direction in the support members 484 and 486. These further slots 483 serve to accomodate particular collimator plates 482 and the specific inclination of any given vertically inclined slot 483 is such as to orient the plate inserted therein approximately along a radius to the x-ray source. The two support means 484, 486 are partially maintained in spatial relationship to one another by a dowel pin 490 which also passes into plate 462.

During fabrication the collimator plates 482 are positioned in the vertically inclined slots 483 and an epoxy resin composition is thereafter flowed along the channels 488 — which then enable such composition to flow within the vertically inclined slots 483 as well, and thereby fix (i.e. following curing) the position of the collimator plates 482.

Detector means 458 comprises a chamber 512 which is completely enclosed except where various electrical feed-throughs, gas valves or gauges or so forth are provided — as hereinbelow will be set forth. Total enclosure is of course necessary, in that the present detector is of the ionization type, i.e. measurements are effected via ionization currents generated in inter-electrode gaps by the x-rays being absorbed in a high Z gas such as xenon, krypton or a xenon-krypton mixture contained in the said gaps at relatively high pressure, typically at 10 atmospheres or more. In particular and referring to the relatively schematic showing of FIG. 4, a series of side-by-side ionization detector cells are created by virtue of alternating high voltage plates 496 and detector plates 498. A pair of such high voltage and detector plates, i.e. defining a detector cell, is actually aligned with a pair of spaced collimator plates 482, so that as already mentioned, the collimated x-ray radiation proceeding between a pair of adjacent collimator plates 482, thence passing directly into the associated detector cell. A total of 301 such detection cells are actually defined within detector means 458.

Figure 5:
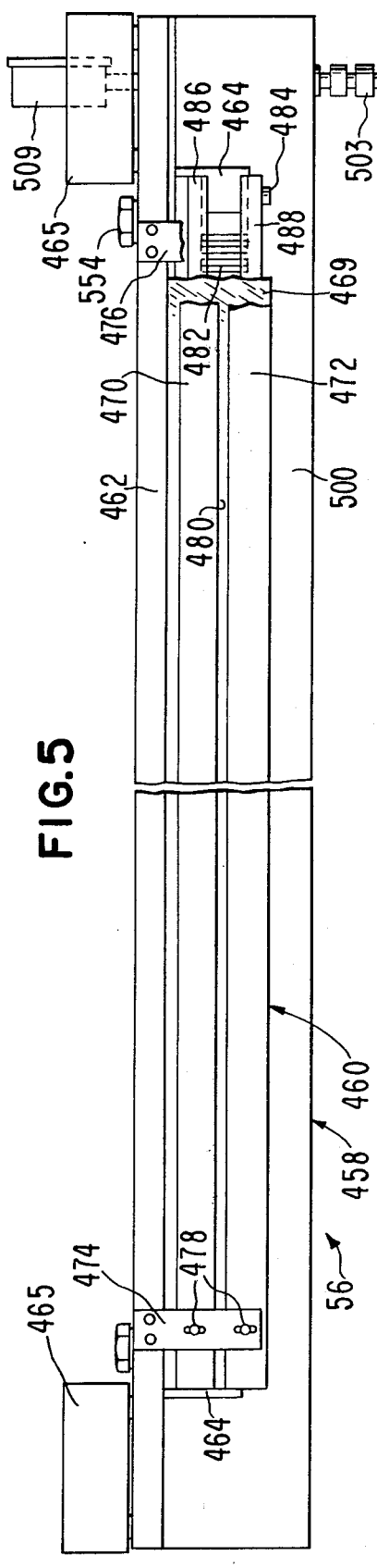
FIG. 5 is a top plan view of the FIG. 4 apparatus.

Referring to the right side, partially broken away view of FIG. 7, it will firstly be noted that the enclosed detector casing 64 is actually defined by a U-shaped shell 500 which is affixed to support plate 462 by means of a plurality of bolts 502. A sealing gasket 504 is provided adjacent the interface between member 500 and plate 462. The gasket 504 may comprise indium wire — which becomes deformed at the interface during joining of member 500 and plate 462. As seen in FIG. 5, a compression adapter 503 and vacuum valve 507, are provided, which enable gas to be introduced, as required, to the interior of the enclosure (i.e. to chamber 512); and similarly a gas pressure gauge 509 is provided for enabling examination of the pressure within chamber 512). A channel 505 constituting a window for the collimated x-rays proceeding toward the detector cells, is also formed lengthwise along one side of the u-shaped shell 500.

A pair of plate support members 508 and 510 extend for most of the length of the chamber 512. The plate support members 508 and 510 comprise an electrically insulating material such as for example a composite fiberglass material or so forth. A bolt 515, one of a pair of such bolts, and a pin 516 support members 508 and 510 in their vertical positioning. It will be noted, however, that some spacing 520 is present adjacent the outside surfaces of each of the support members 508 and 510. Resilient washers 522 may intervene in space 520.

In addition, or in place thereof, the arrangement shown in FIGS. 10 and 11 may be employed for providing a degree of shock absorption between the support members 508, 510 and the adjacent inner metallic walls surrounding chamber 512. Thus, as seen in FIGS. 10 and 11, an extended length of plastic tubing 514, as for example of Teflon, may be passed several times about the outer lateral periphery of members 508 and 510 and spaces 464, with the ends of the said tubing being secured to spacers 464 by means of threaded fasteners 516. The purpose of the aforementioned resilient elements, i.e. tubing 514, and washers 522, is to isolate the array of ionization cells in the present device from mechanical shock, which could act to affect the spacing of the cells, and thereby introduce spurious signals.

The various detector plates 498 and high voltage plates 496 are mounted in their desired positions within support members 508 and 510 by the same technique as has been described with respect to mounting of collimator plates 482. In particular, a series of channels 530 extend lengthwise along the inwardly directed faces of members 508 and 510; and in addition, a series of vertically inclined slots 531 are formed, which intersect the channels 530. These vertically inclined slots function to receive and thereby position the detector and high voltage plates 496 or 498. Thus, of course, the said vertically inclined slots 531 make an angle with the vertical, which increases as one proceeds toward the opposed ends of support members 508 and 510, in that (as already discussed), the detector cells, like collimator plates 482, will be approximately aligned along radii proceeding toward the source of radiation. Thus each of the said detector cells, which is essentially in a form of a parallelepiped, will have its principal axis approximately aligned along such a radius.

The structures of the detector plate 498 and high voltage plate 496 may be better understood by reference to the enlarged view of FIG. 8, and the cross sectional view of FIG. 9 which is taken along the line 9—9 in FIG. 8. It may be seen there that each of the high voltage plates 496 comprises a stainless steel material, typically of about .025 thickness. Each of the plates 496 is connected to the positive side of a high voltage source (schematically indicated at 524 — and typically providing potentials of the order of 500 to 5000 volts) by connections effected at a tab portion 526. Each such tab portion 526 is thus connected via a current limiting resistor 528 and a high voltage bus 532. Connection to high voltage bus 532 as may be seen in FIG. 7, is effected by means of an insulating connector 534, which may be of the "spark-plug" type.

Referring particularly to the cross sectional view of FIG. 9, it will be seen that each detector plate 498 is actually formed of a laminate detector structure 536, which includes a central conductive layer 538, e.g. of copper, on each side of which resides an insulating plastic layer 540, over which are the stainless steel detector plates 498. Thus, it will be clear that it is actually the detector structure 536 which is mounted between any two high voltage plates 496 — whereby any given ionization cell is defined by one of the detector plates 498 carried by such structure 536, together with a spaced high voltage plate 496.

Formed along all lateral edges of the detector plates 498, but spaced therefrom, is a guard ring 542, also of stainless steel. In practice, structure 536 shown in FIG. 9, is formed by photoetching away the portions 544, to leave the spaced guard ring 542. In use guard ring 542 is maintained at a ground potential via connecting tab 555 (as also schematically suggested in FIG. 9) and the signal from each individual cell is taken from the detector plates 498. The spacing between the high voltage plate 496 and the detector plate 498 associated therewith, is typically of the order of 0.100 inches, with the total thickness of structure 536 being only about 0.025 inches.

Structure 536 which includes the aforementioned guard rings 542 and central conductive layer 538, in effect thoroughly shields each detector plate 498, in a manner resembling that which occurs in a coaxial cable; i.e. a ground shield effectively envelopes the conductive signal-carrying detector plate 498. The net effect of this arrangement is to vastly reduce stray capacitance effects or cross-talk between adjacent cells. In consequence, especially in further view of the reduction in physical shock effects which is enabled by the structures previously discussed in connection with FIGS. 10 and 11, the readings provided from the various detection cells are little affected by extraneous electrical activity or by vibration or the like.

The lead-out signals proceeding from each detector plate 498 pass through lead-out wires 550, which pass through insulating sleeves 552 where required. A plurality of such lead-outs then proceed out from casing 494 through a plurality of feed-throughs 554.

While the present invention has been particularly set forth in terms of specific embodiments thereof, it will be understood in view of the present disclosure that numerous variations upon the invention are now enabled to those skilled in the art; which variations yet reside within the scope of the present teaching. Accordingly, the invention is to be broadly construed and limited only by the scope and spirit of the claims now appended hereto.

We claim:

1. Apparatus for examining a bodily portion of a patient by means of penetrating radiation and providing a digital output signal for use in reconstruction of a two-dimensional representation of the bodily structure residing in a thin section taken through said body portion; said apparatus comprising:

an assembly rotatable about an axis extending along a central opening defined there;

means for positioning the portion of said body to be examined within said central opening, whereby said axis of assembly rotation is substantially perpendicular to said section;

a source of penetrating radiation being mounted on said assembly toward one side thereof;

a first collimating means being mounted proximate said source toward said one side of said assembly, said means including a first relatively wide opening toward said source, and a spaced relatively narrow slit aligned with said first opening, the radiation emerging from said slit being in the configuration of a fan beam;

detector means for said radiation positioned on said assembly opposite said source for detecting radiation progressing laterally across said section and not absorbed by said body portion;

means for rotating said assembly whereby said fan beam impinges upon said body portion at a plurality of incident directions:

signal processing and conditioning means mounted on said assembly and movable therewith, for receiving the output signals from said detector means and amplifying and converting said signals to digital form; and first interconnection means for receiving the outputs from said signal processing and conditioning means and enabling interfeed of said digitalized output signals to an image reconstruction station.

2. Apparatus in accordance with claim 1, wherein the opening in said spaced slit is adjustable to at least in part enable variation in the thickness of said fan beam.

3. Apparatus in accordance with claim 2, wherein said slit may be opened sufficiently to enable a radiation pattern to be rendered incident on said patient over an extended area, to thereby enable a conventional x-ray radiograph.

* * * * *